US012335665B2

(12) United States Patent  
Miller et al.

(10) Patent No.: US 12,335,665 B2
(45) Date of Patent: Jun. 17, 2025

(54) VIDEO PROJECTION-BASED DISTRACTION THERAPY SYSTEM FOR RADIATION THERAPY

(71) Applicant: The Regents of the University of Colorado, Denver, CO (US)

(72) Inventors: Brian W. Miller, Aurora, CO (US); Douglas Holt, Aurora, CO (US); Brian D. Kavanagh, Greenwood Village, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 176 days.

(21) Appl. No.: 17/609,448

(22) PCT Filed: May 7, 2020

(86) PCT No.: PCT/US2020/031871
§ 371 (c)(1),
(2) Date: Nov. 8, 2021

(87) PCT Pub. No.: WO2020/227528
PCT Pub. Date: Nov. 12, 2020

(65) Prior Publication Data
US 2022/0217312 A1    Jul. 7, 2022

Related U.S. Application Data
(60) Provisional application No. 62/844,394, filed on May 7, 2019.

(51) Int. Cl.
H04N 9/31      (2006.01)
A61N 5/10      (2006.01)
(Continued)

(52) U.S. Cl.
CPC ........... *H04N 9/317* (2013.01); *A61N 5/1077* (2013.01); *G02B 27/0081* (2013.01);
(Continued)

(58) Field of Classification Search
CPC .. H04N 21/214; H04N 21/2143; H04N 9/317; A61N 5/1077; A61N 2005/1092; G02B 27/0081; G02B 27/145; H04B 7/15
See application file for complete search history.

(56) References Cited

U.S. PATENT DOCUMENTS 5,134,373 A      7/1992   Tsuruno et al.
5,400,069 A  *   3/1995   Braun .................... H04N 7/144
                                                        359/454
(Continued)

FOREIGN PATENT DOCUMENTS

WO    WO-2016195684    *  12/2016

OTHER PUBLICATIONS

AAPM, "MedPhys 3.0—Watching Videos Helps Kids Avoid Anesthesia During Radiation Therapy," https://www.aapm.org/MedPhys30/articles/VideosKids.asp, 1 page, Feb. 27, 2019.
(Continued)

Primary Examiner — Yassin Alata

(57) ABSTRACT

Various embodiments of the present technology are generally related to a multimedia distraction system for patients receiving external beam radiation therapy. More specifically, some embodiments relate to a system for providing a video image to a patient while undergoing a treatment to avoid the need to anesthetize. The system comprises a video image source, a projector communicatively coupled to the video image source, abeam expander coupled to the projector, and a screen transparent to the radiation beam used in a radiation therapy treatment. The present technology can be used to distract a patient during multiple types of external beam
(Continued)

radiation therapy including three-dimensional conformal radiation therapy, intensity-modulated radiation therapy, volumetric modulated arc therapy, and non-coplanar arcs, without interfering with the treatment.

20 Claims, 9 Drawing Sheets

(51) Int. Cl.
    *G02B 27/00*     (2006.01)
    *G03B 21/14*     (2006.01)
    *G03B 21/62*     (2014.01)
    *H04B 7/15*     (2006.01)

(52) U.S. Cl.
    CPC ........... *G03B 21/145* (2013.01); *G03B 21/62* (2013.01); *H04B 7/15* (2013.01); *A61N 2005/1092* (2013.01)

(56) References Cited

U.S. PATENT DOCUMENTS

| | | | | |
|---|---|---|---|---|
| 5,877,732 | A * | 3/1999 | Ziarati | A61B 5/055 600/418 |
| 6,388,821 | B1 * | 5/2002 | Dehmlow | G02B 13/22 359/716 |
| 6,774,929 | B1 | 8/2004 | Kopp | |
| 7,173,766 | B2 * | 2/2007 | Kimura | G02B 13/22 359/676 |
| 7,384,158 | B2 * | 6/2008 | Ramachandran | G02B 17/06 353/77 |
| 8,339,524 | B2 * | 12/2012 | Chien | H04N 9/641 348/839 |
| 9,438,869 | B2 | 9/2016 | Gillies et al. | |
| 2005/0283068 | A1 * | 12/2005 | Zuccolotto | G01R 33/283 600/410 |
| 2010/0309439 | A1 * | 12/2010 | Bi | H04N 9/3161 353/30 |
| 2013/0047188 | A1 * | 2/2013 | Perlman | H04B 7/18517 725/64 |
| 2017/0046577 | A1 * | 2/2017 | Rocque | A61B 5/1115 |
| 2017/0209110 | A1 | 7/2017 | Kiraly | |

OTHER PUBLICATIONS

International Application No. PCT/US2020/031871, International Search Report & Written Opinion, 11 pages, Aug. 4, 2020.

Stanford University et al., "Avatar Setup Guide," https://sites.google.com/view/stanford-avatar/hom/avatar-guides/avatar-setup-guide, 12 pages, Feb. 27, 2019.

* cited by examiner

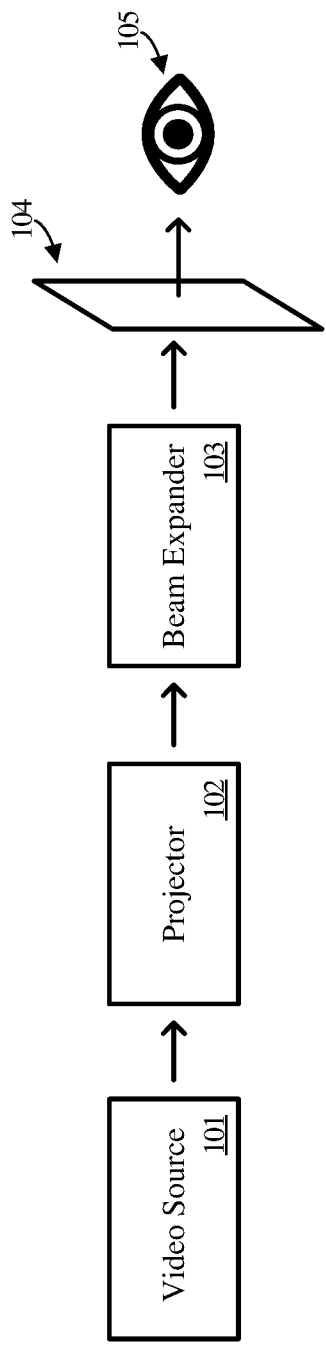

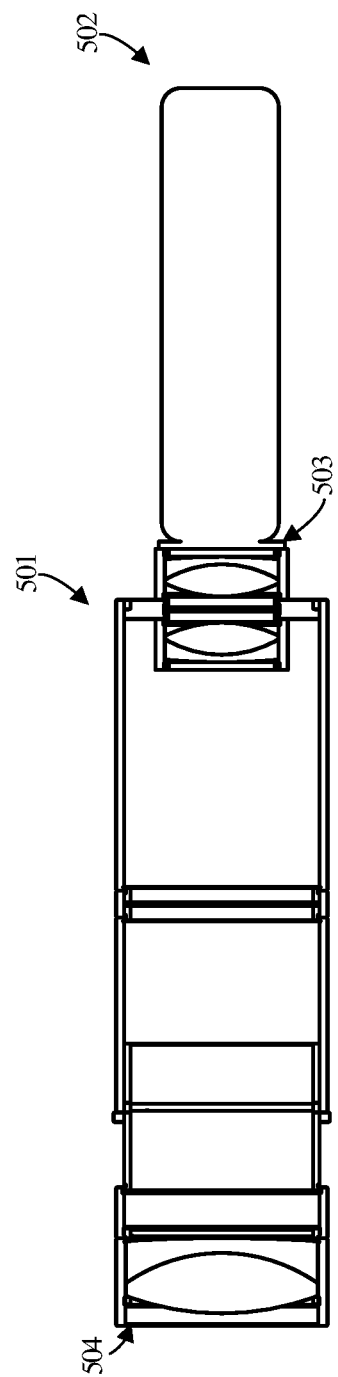

VIDEO PROJECTION-BASED DISTRACTION THERAPY SYSTEM FOR RADIATION THERAPY

CROSS-REFERENCE TO RELATED APPLICATIONS

This Application is related to and claims priority to U.S. Provisional Patent Application No. 62/844,394, entitled "VIDEO PROJECTION-BASED DISTRACTION THERAPY SYSTEM FOR RADIATION THERAPY," filed on May 7, 2019, which is incorporated by reference herein in its entirety.

TECHNICAL FIELD

Various embodiments of the present technology generally relate to distraction therapy for patients. More specifically, some embodiments relate to a system for displaying a video image for a patient during radiation therapy treatments.

BACKGROUND

Radiation therapy treatment is used on patients of all ages for treatment of illnesses including different forms of cancer and cancerous tumors. External beam radiation therapy is commonly used on pediatric patients diagnosed with brain tumors. For pediatric patients, it may be difficult or nearly impossible to remain still and calm throughout the entirety of a treatment, as treatments can last several hours. For this reason, children receiving external beam radiation therapy are often anesthetized for the procedure to reduce movement or anxiety. Children undergoing these radiation therapy treatments are often treated on a regular basis, sometimes on multiple occasions in the same day. Frequent anesthetizing of pediatrics patients can cause adverse side effects risking the patient's health or overall quality of life.

During radiation therapy treatment, it is integral that the radiation beam is not interfered with. Interfering with a radiation beam can cause adverse reactions in a number of ways. Providing distractions during therapy treatments such as external beam radiation therapy has proven to be a successful approach to avoiding the use of anesthesia in pediatric and adult patients who have difficultly remaining still or calm for extended periods of time. Thus, providing a mechanism that can distract a patient during radiation therapy treatment can reduce costs of the procedure and improve a patient's overall health and experience. Distraction-based approaches may be extendable to any patient undergoing a similar therapy treatment.

It is with respect to this general technical environment that aspects of the present technology disclosed herein have been contemplated. Furthermore, although a general environment has been discussed, it should be understood that the examples described herein should not be limited to the general environment identified in the background.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Various embodiments herein relate to systems, methods, and software for a multimedia distraction system for patients receiving external-beam radiation therapy. In some embodiments, the systems, methods, and software implement a long throw video image onto a radio-transparent screen which a patient views during treatment. The present technology accommodates any type of linear acceleration (LINAC) based radiotherapy treatment. In the present technology, a projection system is placed at a location where it will not perturb a radiation beam during treatment. In an exemplary implementation, the present technology is used in pediatric cases in which the patient receives radiation treatment on a regular basis. Traditionally, anesthesia is used on young patients during treatment because they are required to remain still for extended periods of time. However, the present technology is extendable to all patients and is not limited to pediatric care. The present technology may eliminate the need for certain patients to receive anesthesia on a regular basis during treatments. The present technology is applicable for several other uses including distraction-based therapy used to reduce anxiety or movement during a radiation therapy procedure.

In an embodiment of the present technology, a system comprises a video source, a projector communicatively coupled to the video source, wherein the projector is configured to receive video content from the video source and emit a projection of the video content, and a beam manipulator comprising multiple lenses configured to focus the projection of the video content onto a first side of a screen, wherein the video content can be viewed on a second side of the screen. The system may further comprise the screen, wherein the screen is a radio-transparent screen mounted above a radiation therapy couch and emanates the projected video content to the second side of the screen. In some examples the system further comprises at least one set of wireless repeaters configured to communicate the video content from the video source to the projector, wherein the video source is located outside of a radiation therapy room and the projector is located inside of the radiation therapy room. Furthermore, the system may comprise an adjustable projector housing comprising a proximal end and a distal end, wherein the distal end comprises a means for attaching the projector and proximal end comprises a clamp for securing the adjustable housing in a radiation therapy room. The projection of the video content may comprise a long-throw video image and the projector may be located at a location where the projector will not perturb a radiation beam during radiation therapy. The multiple lenses of the beam manipulator may comprise at least one set of achromatic doublets and can be configured to flip the projection of the video content such that the video content can be viewed in a non-reversed fashion on the second side of the screen. In certain examples, the projector is a pico projector and the beam manipulator comprises a beam expander and is attached to an output lens of the projector.

In another embodiment of the present technology, a video image projection system comprises: a projector, wherein the projector is located at a location where it does not interfere with radiation beams during radiation therapy and is configured to receive video image from a video source and project the video image onto a first lens of a beam manipulator; the beam manipulator comprising multiple lenses, wherein the beam manipulator is configured to focus the video image based on a distance to create a modified video image and emit the modified video image onto a first side of a radio-transparent screen; and the radio-transparent screen, wherein the radio-transparent screen is separated from the beam manipulator by the distance and the modified video image is viewable on a second side of the radio-transparent screen.

In yet another embodiment of the present technology, a method of operating a video projection system comprises, in response to receiving video content from a video content source, projecting the video content, manipulating an image associated with the video content such that the image is focused on a first side of a screen located a distance away from a projector, and providing the video content in on a second side of the screen such that the video content can be viewed in a non-reversed fashion on the second side of the screen.

While multiple embodiments are disclosed, still other embodiments of the present technology will become apparent to those skilled in the art from the following detailed description, which shows and describes illustrative embodiments of the technology. As will be realized, the technology is capable of modifications in various aspects, all without departing from the scope of the present technology. Accordingly, the drawings and detailed description are to be regarded as illustrative in nature and not restrictive.

BRIEF DESCRIPTION OF THE DRAWINGS

Many aspects of the disclosure can be better understood with reference to the following drawings. The components in the drawings are not necessarily drawn to scale. Moreover, in the drawings, like reference numerals designate corresponding parts throughout the several views. While several embodiments are described in connection with these drawings, the disclosure is not limited to the embodiments disclosed herein. On the contrary, the intent is to cover all alternatives, modifications, and equivalents.

FIG. 1 illustrates a video-based distraction therapy system in accordance with some embodiments of the present technology.

FIG. 5A illustrates an example of a pico projector coupled to a beam expander in accordance with some embodiments of the present technology.

Figure 2A:
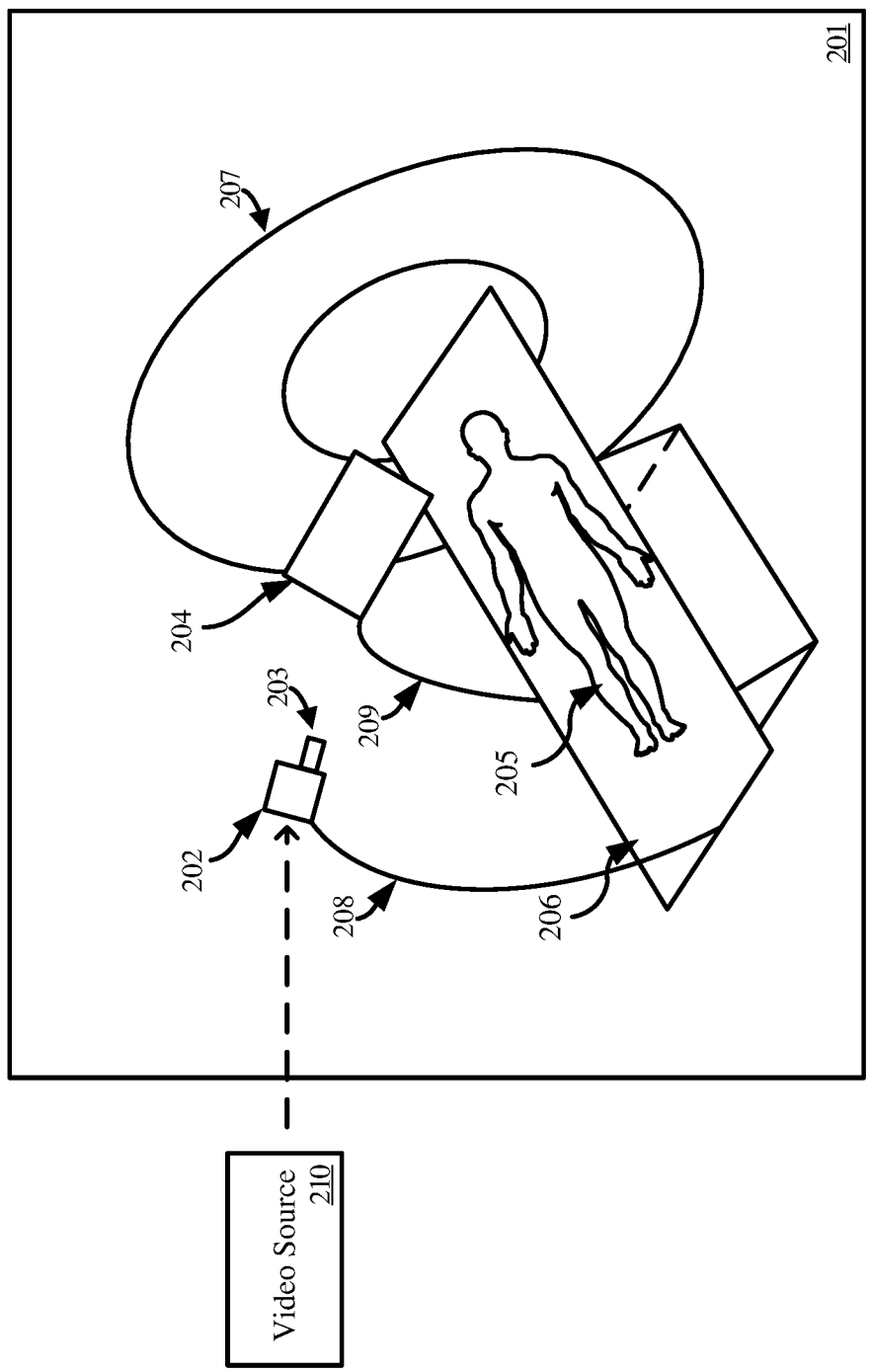
FIG. 2A illustrates an exemplary environment in accordance with some embodiments of the present technology.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

The following description and associated figures teach the best mode of the invention. For the purpose of teaching inventive principles, some conventional aspects of the best mode may be simplified or omitted. The following claims specify the scope of the invention. Note that some aspects of the best mode may not fall within the scope of the invention as specified by the claims. Thus, those skilled in the art will appreciate variations from the best mode that fall within the scope of the invention. Those skilled in the art will appreciate that the features described below can be combined in various ways to form multiple variations of the invention. As a result, the invention is not limited to the specific examples described below, but only by the claims and their equivalents.

Various embodiments of the present technology generally relate to multimedia distraction systems for patients receiving external beam radiation therapy. More specifically, some embodiments relate to a system comprising a video image source, a projector, and a radio-transparent screen through which a video image can be displayed for a patient to watch during a radiation therapy treatment. The projector projects a long-throw video image onto a radio-transparent screen that the patient can view during treatment. The present technology may be used with a variety of treatments including three-dimensional conformal radiation therapy (3D CRT), intensity-modulated radiation therapy (IMRT), volumetric modulated arc therapy (VMAT), and non-coplanar arcs, without interfering with the treatment.

Various embodiments of the present technology can create a streamlined process regarding how content is delivered to a patient during radiation therapy treatment. During radiation therapy treatment, it is integral that a distraction-based therapy system does not interfere with radiation beams that are to be received by the patient. Additionally, it is of great important not to disrupt the workflow within a radiation therapy room, allowing doctors, nurses, and other administrators of radiation therapy to work in an efficient, undisturbed manner.

Distraction-based therapy is of great value to patients undergoing radiation therapy treatments. In many cases a patient must undergo radiation therapy treatments on a regular basis, which can include receiving a series of multiple radiation therapy treatments in a single day. Typically, radiation treatments for children or adults can last from 30 minutes to two hours. Research indicates that treatments longer than 30 minutes can be challenging for both children and adults because it may create a high-anxiety environment and a patient may have a hard time remaining still for extended periods of time. Especially in children, anesthesia may be used on the patient during long treatments to mitigate movement and anxiety. However, children and adults may be exposed to unnecessary health risks when subjected to anesthesia on a regular basis.

A majority of pediatric brain tumor treatments are treated with non-coplanar arcs. Therefore, the present technology accommodates non-coplanar beam treatments used for certain treatments. By developing a system that does not interfere with radiation treatment including non-coplanar arcs (especially treatments for the brain), patients may be exposed to less anesthesia and have a healthier radiation therapy treatment experience.

The present technology diminishes the need for anesthesia in patients by providing a visual distraction for the patient. In some embodiments, the visual distraction is a movie or TV show. In other embodiments, the visual distraction may comprise a video or image displaying instructions, cues, or other visual information to a patient. In some implementations, a movie or other form of video image may begin when a patient is positioned for treatment without disrupting the therapist.

Certain embodiments of the present technology include a projector mounted on an adjustable arm. The adjustable arm may attach to an end of a radiation treatment couch inside a radiation therapy room, in some examples. The end of the couch may be the foot of the couch, the farthest end away from the radiation side of the table, or an alternative side of the couch. The projector, in some embodiments, uses a lens to project an image with a low divergence throw ratio onto a small screen located above a patient's head at the opposite side of the radiation treatment couch. The screen may additionally be mounted to an adjustable arm (e.g., having a series of adjustable pivots points allowing for custom curvatures and positioning of the end with the projector). In some embodiments, the adjustable arm may be mounted on an opposite end of the couch from the projector.

Some embodiments of the present technology allow any site on a patient's body to be treated without the need to change planning or treatment related to the patient in order to accommodate the projector or screen. For example, the moveable arms may be clamped to the couch via an operating room clamp, allowing for their attachment and removal, thus avoiding any internal changes to the couch. In some embodiments, the flexible arm attached to the projector or screen may comprise sliding rods to shorten or extend them to an ideal location.

The projector may be in communication with a video image source. In certain embodiments, the video image source is located outside of the radiation therapy room. In some scenarios, a radiation therapy room may be impermeable to wireless signals such as Wi-Fi or Bluetooth signals. Thus, the video image source may be located outside of the radiation therapy room to allow the video image source to receive video image content. The projector and video image source may be in communication via wireless HDMI transmitters and receivers, eliminating interference during treatment. In some embodiments, the video image source could comprise an Apple® TV. In some embodiments, the video image source may have access to a library of video images through a web-based streaming service such as Netflix®, Hulu®, or any other form of video image library stored online or a non-transitory storage device. In addition, the video image source may be provided through an over-the-air broadcast high definition television signal (HDTV), satellite television broadcast signal, coaxial cable television signal, on-demand video streaming, video or other media files stored on a local storage device, or any other source capable of providing video image content.

In some embodiments, the video image source may be located inside the radiation therapy room, such as mounted on a radiation machine. In the present embodiment, the video image source may be accessible to a doctor, nurse, or other therapist from inside the room. In this manner, the therapist may manipulate video content projected for the patient to watch directly from inside the room.

In certain embodiments, a patient may provide the video image source with a video image of their choice. For example, patients may save their position in a video image, such as a movie they are in the middle of watching, to continue the video image from where they left off. This may be exceptionally useful for patients undergoing multiple treatments in a single day, allowing them to continue their movie or show each time they are back in the radiation therapy room. In alternative embodiments, a therapy session may provide visual assistance to a patient during a treatment or procedure. For example, a procedure may require that a patient hold their breath during periods of time or may need to be instructed to breathe at other periods of time. The present technology includes the ability to provide video feedback or cues to a patient during a procedure through the projection of an assistive video or image.

In some embodiments, the projector may alternatively be installed into a radiation therapy room in a more permanent fashion. Alternative methods of installation allow the projector to be hard-wired into the room, allowing for direct, wired communication with a video image source. The hard-wired system may further eliminate complications related to communicating with the projector from outside a radiation therapy room including poor connection.

The present technology implements an ultra-throw lens that, in certain implementations, may throw an image six feet in distance for one foot in horizontal width, for example. Note that the throw distance to horizontal width ratio may differ in various implementations, and any other throw distance and horizontal width for the projected image is possible and within the scope of this disclosure.

The lens system of the present technology comprises an afocal system comprising multiple lenses (e.g., three, four, or more) that expand the beam thus changing the projection magnification. Additional lenses may be added to invert and/or revert the image. Some embodiments perform the optical modifications (e.g., magnification, inversion, reversion and the like) as a built-in projector feature. Other embodiments realize these features optically.

In some scenarios, a therapist may adjust the focus of the image for a given radiation therapy setup. The lens system reduces common issues with high-magnification lens systems including vignetting and cropping. Vignetting is a phenomenon causing a reduction in brightness or color on the periphery of an image. The lens system comprises achromatic doublets designed to reduce the effect of chromatic and spherical aberration. Aberration is a property of optical systems that causes light to spread out over a region of space rather than focusing to a point. Aberration causes an image to appear blurred or distorted.

In an exemplary embodiment of the present technology, the projector used to project a video or image for distraction-based therapy is a pico projector. A pico projector is a small hardware device designed to project content (e.g., from a video source such as a smartphone, camera, tablet, notebook or memory device) onto a wall or other flat surface (e.g., a screen). Pico projectors may also be referred to as pocket, handheld or mobile projectors. As such, the use of a pico projector in various embodiments allows ease of mounting on a flexible mounting rod or device.

In accordance with various embodiments, a pico projector allows the device to be small enough that it is easily manipulated and moved according to a given therapy scenario. The projector of the present technology can be coupled to a beam expander to project the video image on the screen. The beam expander is a lens-based system that projects over a long throw distance compared to a small screen size. The beam expander may include an afocal system that uses a short focal length lens (closest to the projector) and a longer focal length lens at the end towards the screen. The ratio of the focal lengths gives the magnification (beam expansion) and amount by which the projection image size can be reduced. The lenses can be optimized to reduce aberrations, distortion, and vignetting. The projection image can also be inverted and reverted optically (with a more complex lens system), but this can also be achieved with software for some projectors.

A beam expander is an optical system used to increase or decrease beam diameter. More specifically, a beam expander may increase the diameter of a collimated input beam to create a larger collimated output beam. The beam expander of the present technology is coupled to the long throw projector and optimizes each image or video for the screen.

The achromatic lenses of the present technology are designed such that they bring two wavelengths into focus in the same plane. An achromatic doublet is composed of two individual lenses wherein each lens is made with glass that provides a different amount of light dispersion. One lens in the achromatic doublet is concave (negative) with relatively high dispersion, while the other lens is convex (positive) with lower dispersion. The lenses in an achromatic doublet are set up such that the positive power of the convex lens is not quite equaled by the negative power of the concave lens. When light passes through the achromatic doublet, the lenses operatively form a weakly positive lens that is capable of bringing two different wavelengths of light to a common focus.

The lens design of the present technology effectively minimizes pincushion and barrel distortion in the projected image. Pincushion distortion is a common phenomenon in which the perimeter of an image is magnified more than the center. Barrel distortion is another common phenomenon in which the center of an image is magnified more than the perimeter. Compared to what is seen when using the projector alone, the projection image when using a lens is flipped upside down. Flipping the image back up and reverting (mirroring) it can be achieved on some projectors in their software menu (rear projection mode) or can be achieved optically using a prism or relay lens.

In some embodiments, the projector may be equipped with a battery pack, allowing it to be easily moved around or adjusted. In other embodiments, the projector may be wired to a power source, such as in the hard-wired scenario previously discussed. In some embodiments, the technology described herein may be built by a manufacturer incorporate various design features to achieve a long throw ratio. As such, these custom projectors would not need a custom lens design. In addition, some embodiments may use a paper-thin, flexible organic light-emitting diode (OLED) as a substitute for the projector and screen system.

The present technology comprises a screen used to display a video image to a patient. A screen in a radiation therapy room should not distort radiation and thus cannot be any thicker than a thick piece of paper or plastic. Interference in radiation treatment can cause damage to the patient, the treatment machine, the screen, or additional components, as the screen will likely be placed in a radiation field while a patient watches the screen overhead. For this reason, the present technology is designed to project onto the back of a thin screen, while a patient views the video on the front of the screen. In some embodiments, the screen is a radio-transparent screen, making it transparent to radio-frequency waves used during radiation therapy.

FIG. 1 illustrates an example of the present technology in a radiation therapy environment. FIG. 1 includes video source 101, projector 102, beam expander 103, screen 104, and viewer 105. In the present example, video source 101 provides a video image to projector 102. Projector 102 projects the video image into beam expander 103. Beam expander 103 projects a modified video image onto a first side of screen 104. Viewer 105 views the modified video image on a second side of screen 104. In some embodiments, video source 101 is located outside of the radiation therapy room. In alternative embodiments, video source 101 may be mounted inside the radiation therapy room. Projector 102 may comprise a pico projector in certain embodiments. Projector 102 is operatively coupled with beam expander 103. Beam expander 103 comprises a series of lenses which flip the video image for projection onto the back of screen 104 and focus the video image onto screen 104. Screen 104 is a radio-transparent screen in some embodiments. Screen 104 may be mounted above a patient's head for viewing during radiation therapy treatment. Screen 104 may be transparent to multiple types of radiation therapy treatment including 3D CRT, IMRT, VMAT, and non-coplanar arcs. Viewer 105 is a patient undergoing radiation therapy in the present example. Viewer 105 may be a pediatric patient who may otherwise need to be anesthetized during radiation therapy treatment. The present technology reduces the need to anesthetize patients by providing a video-based distraction for a patient to watch during a radiation therapy treatment.

FIG. 2A illustrates an example environment in which some embodiments of the present technology may be utilized. FIG. 2A includes room 201 and video source 210. Room 201 represents any radiation therapy room in which a patient may view a video image during radiation therapy treatment. Video source 210 may be any video image source in communication with pico projector 202 including video source 210. Room 201 comprises beam expander 203, screen 204, patient 205, couch 206, radiation therapy machine 207, adjustable projector arm 208, and adjustable screen arm 209.

In the present example, video source 210 is located outside of the radiation therapy room. Video source 210 may be in communication with pico projector 202 via wireless HDMI repeaters or similar connectivity means in some examples. Pico projector 202 may be any projector capable of being mounted to an adjustable arm on couch 206 and projecting a video image onto beam expander 203. Beam expander 203 flips the video image and focuses the video image onto screen 204. Screen 204 may be a radio-transparent screen. In some implementations, screen 204 represents screen 104.

Patient 205 views the screen from couch 206. In some implementations, patient 205 is provided a video image to the video source prior to treatment. Couch 206 may be any patient table on which a patient receives radiation therapy treatment. Radiation therapy machine 207 may be any radiation therapy machine capable of providing radiation therapy to patient 205 inside room 201. Examples of radiation therapy provided by radiation therapy machine 207 include 3D CRT, IMRT, VMAT, and non-coplanar arcs. Adjustable projector arm 208 holds pico projector 202 in position for projecting onto screen 204 through beam expander 203. Adjustable projector arm 208 may comprise extendable rods for lowering or heightening pico projector 202. Adjustable screen arm 209 may comprise some or all of the same features as adjustable projector arm 208, with the exception of mounting screen 204 instead of pico projector 202.

Figure 2B:
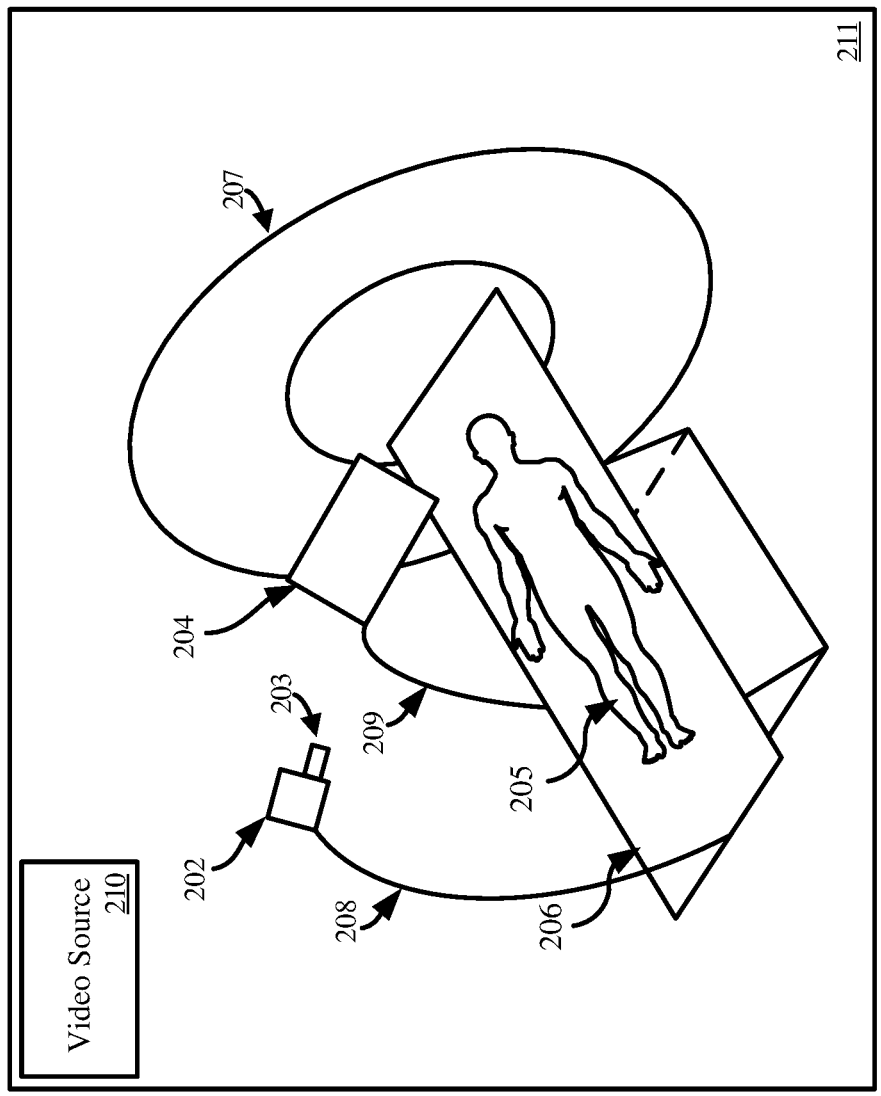
FIG. 2B illustrates an alternative environment in accordance with some embodiments of the present technology.

FIG. 2B illustrates an alternative example environment in accordance with some embodiments of the present technology. FIG. 2B illustrates room 211. Room 211 comprises similar components including pico projector 202, beam expander 203, screen 204, patient 205, couch 206, radiation therapy machine 207, adjustable projector arm 208, and adjustable screen arm 209. Room 211 optionally comprises video source 210. In the present example, video source 210 may be mounted inside room 211, including on radiation therapy machine 207. Mounting video source 210 inside room 211 may allow a therapist to control video source 210 from inside the room. In some examples, a therapist may control video source 210 to play the video image for the patient. In some examples, the video source is a movie.

Figure 3:
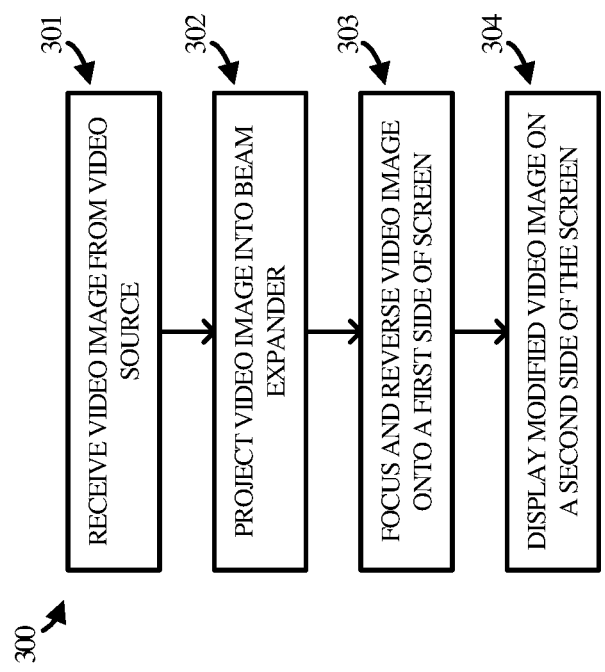
FIG. 3 illustrates a series of steps for video-based distraction therapy in accordance with some embodiments of the present technology.

FIG. 3 illustrates a series of steps 300 in accordance with some embodiments of the present technology. In step 301, projector 102 receives a video image from a video source (e.g., video source 101). In step 302, projector 102 projects the video image into a receiving end of a beam expander (e.g., beam expander 103). In step 303, the beam expander focuses and reverses the video image onto a first side of a screen (e.g., screen 104), wherein screen 104 is a radio-transparent screen in some embodiments. In step 304, a modified video image is displayed on a second side of the screen. In some examples, the modified image comprises a flipped version of the original video image. The modified video image may then be viewed by a patient on the second side of the screen.

Figure 4:
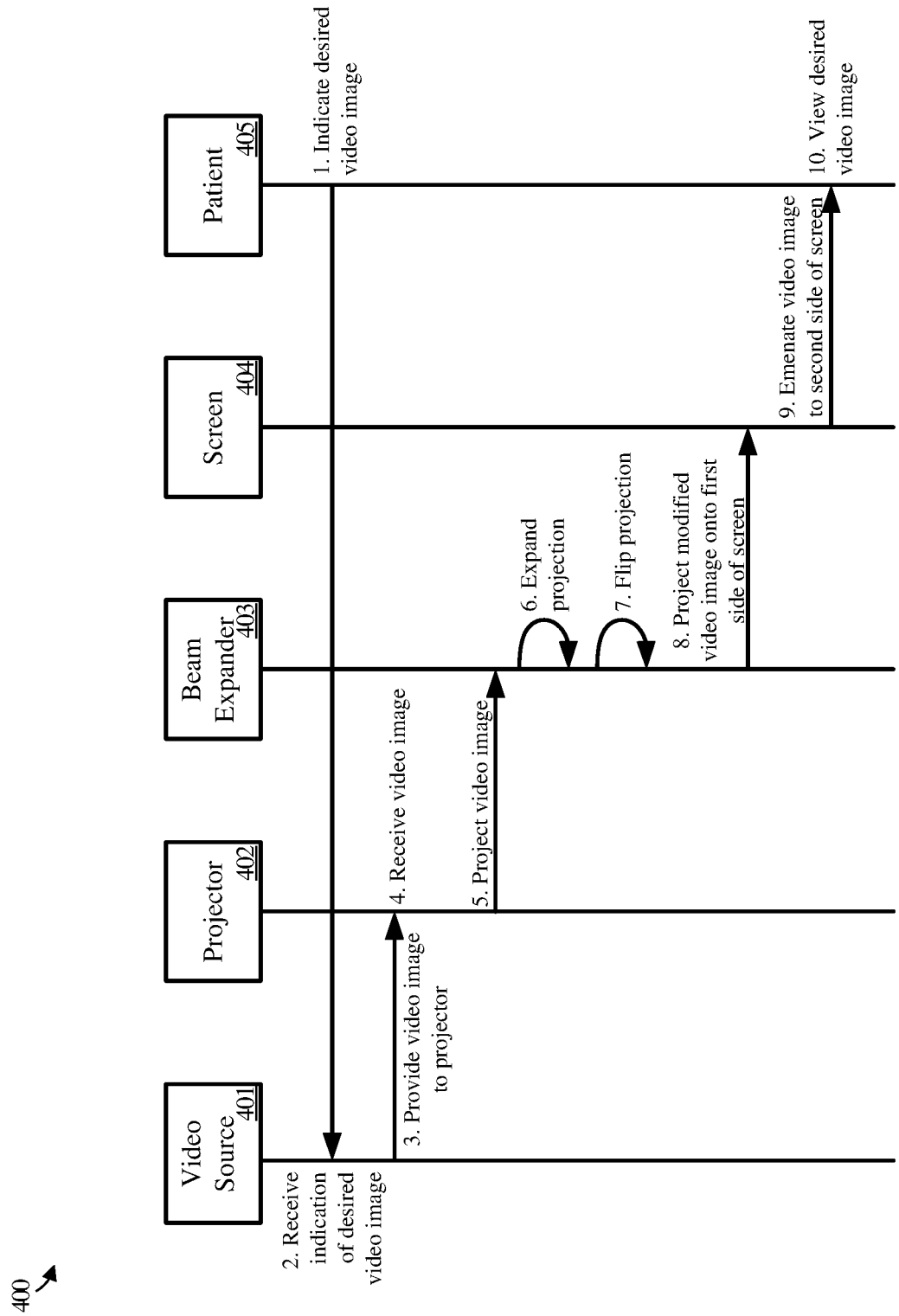
FIG. 4 illustrates a flow diagram in accordance with some embodiments of the present technology.

FIG. 4 is a flow diagram illustrating a series of steps performed in radiation therapy environment 400 in accordance with certain embodiments of the present technology. Radiation therapy environment includes video source 401, projector 402, beam expander 403, screen 404, and patient 405. In step 1, patient 405 provides an indication of a desired video image to watch during a radiation therapy procedure. For example, the patient may select a desired video image from a menu or streaming service, or may provide the video image file to the therapist. In other scenarios, the therapist may select a video image file for the patient to view or a video image may be chosen automatically, as just a few examples. In step 2, video source 401 receives the indication of the desired video image. In some examples, video source 401 receiving the indication of the desired video image could include uploading or transferring the video image file to a local storage device of video source 401 or attaching a removable storage device comprising the desired video file to video source 401. In other examples, video source 401 may receive the indication of the desired video image and responsively communicate with a video server over a communication network or connection to retrieve or stream the video image data over a data network. Other techniques of receiving the desired video image by video source 401 are possible and within the scope of this disclosure.

In step 3, video source 401 provides the video image to projector 402, wherein the video image may be provided through a series of repeaters (i.e., wireless or wired repeaters) or an alternative communication means in some embodiments. In some implementations, wireless repeaters are HDMI transmitters and receivers. In step 4, projector 402 receives the video image. In step 5, projector 402 projects the video image onto a receiving end of beam expander 403.

In step 6, beam expander 403 expands the projection for display using achromatic doublets. In some embodiments the amount of beam expansion may be modifiable by having the first lens group of two shorter afocal lenses on a movable mount where the spacing between the two front group of lenses can be changed (effectively changing the power or focal length of the front group) to create a variable beam expander using mechanisms utilized in zoom lenses or similar.

In step 7, beam expander 403 flips the projection. For example, in the present embodiment, the image is inverted by the beam expander and so the projector software must flip the projection upright for viewing. In alternative embodiments, the image may not need to be flipped upon leaving the beam expander or may be flipped using an alternative means, including passive (i.e., optically) or active means (i.e., computer/software). In the present implementation, a rear projector design is used in which the image is reverted (i.e., flipped horizontally) by software executed within the projector. In some implementations, reverting the image may be achieved optically using a prism, relay lens, or similar means to flip the image. In step 8, beam expander 403 projects a modified version of the video image onto a first side of screen 404. In step 10, screen 404 receives the modified video image on a first side of screen 404. In step 11, the video image emanates to a second of screen 404. In step 12, patient 405 may view the desired video image during a radiation therapy procedure.

Figure 5B:
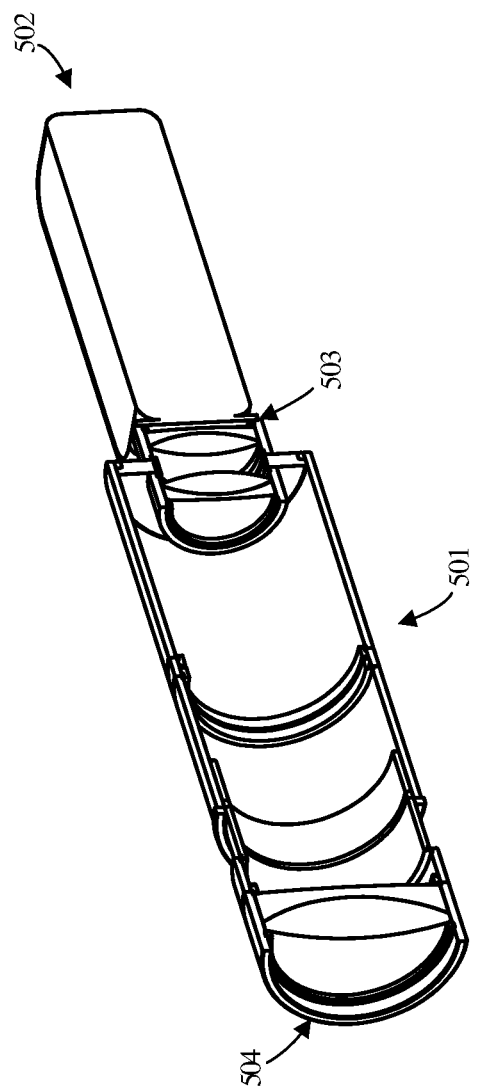
FIG. 5B illustrates an alternative view of the pico projector coupled to the beam expander in accordance with some embodiments of the present technology.
Figure 5C:
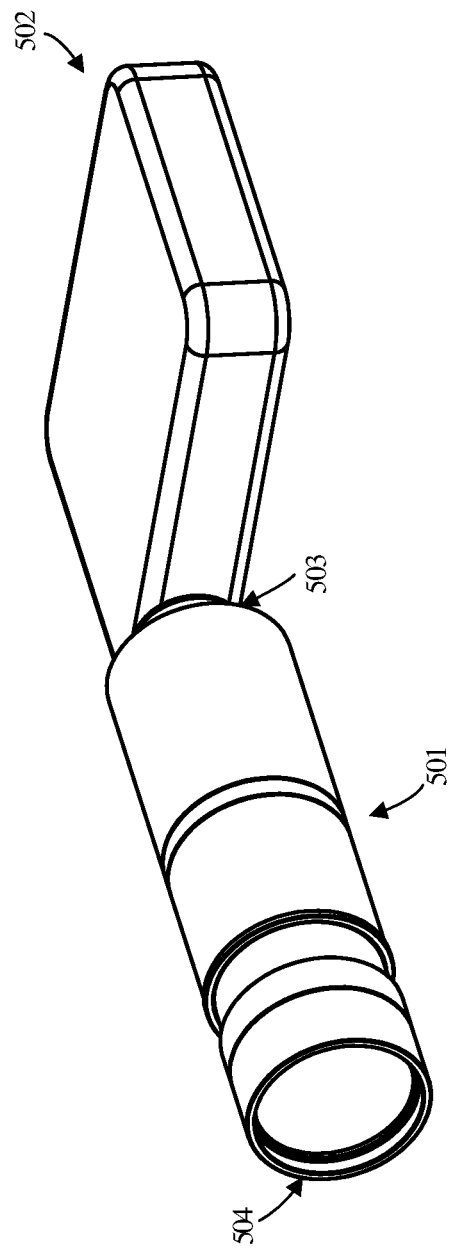
FIG. 5C illustrates an alternative view of the pico projector coupled to the beam expander in accordance with some embodiments of the present technology.

FIGS. 5A-5C depict various views of an exemplary setup of a beam expander (beam expander 501) coupled with a pico projector (projector 502), in accordance with an exemplary embodiment of the present technology. Projector 502 may be an example of projector 102 or pico projector 202. Projector 502 projects a received video image into receiving end 503 of beam expander 501. Receiving end 503 and projection end 504 comprise achromatic lenses of an afocal system with focal length ratios such that the expanded projection exiting projection end 506 beam will result in a smaller projection image or an overall projection system with a significantly increased throw ratio.

Aspects and implementations of the radiation therapy distraction system of the disclosure have been described in the general context of various steps and operations. A variety of these steps and operations may be performed by hardware components or may be embodied in computer-executable instructions, which may be used to cause a general-purpose or special-purpose processor (e.g., in a computer, server, or other computing device) programmed with the instructions to perform the steps or operations. For example, the steps or operations may be performed by a combination of hardware, software, and/or firmware.

Figure 6:
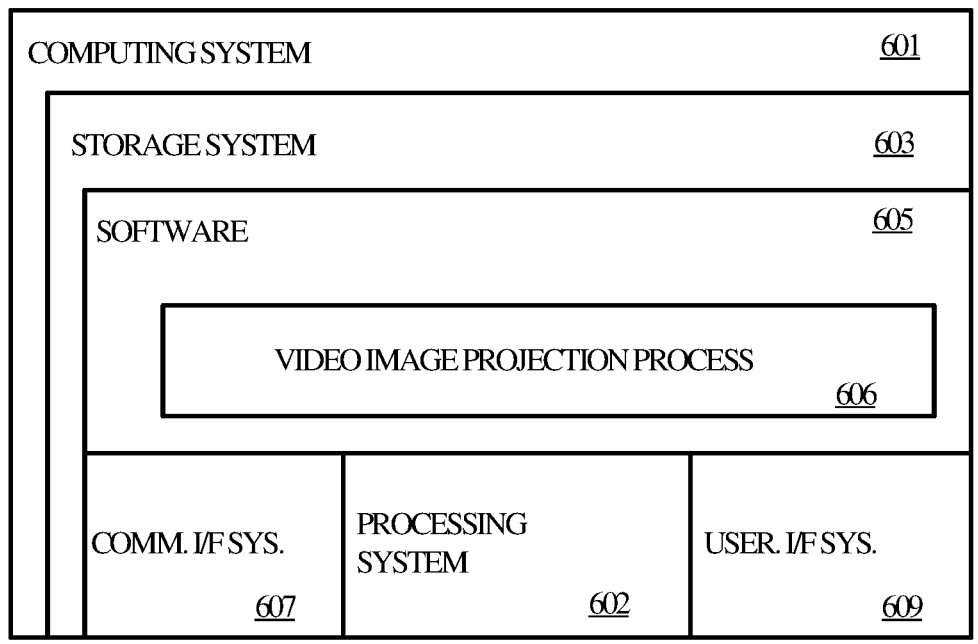
FIG. 6 is a block diagram illustrating an example computing environment that may be used to implement aspects of the present technology.

FIG. 6 illustrates computing system 601 to perform video image projection according to an implementation of the present technology. Computing system 601 is representative of any system or collection of systems with which the various operational architectures, processes, scenarios, and sequences disclosed herein for distraction-based radiation therapy may be employed. Computing system 601 may be implemented as a single apparatus, system, or device or may be implemented in a distributed manner as multiple apparatuses, systems, or devices. Computing system 601 includes, but is not limited to, processing system 602, storage system 603, software 605, communication interface system 607, and user interface system 609 (optional). Processing system 602 is operatively coupled with storage system 603, communication interface system 607, and user interface system 609.

Processing system 602 loads and executes software 605 from storage system 603. Software 605 includes and implements video image projection process 606, which is representative of the video image projection processes discussed with respect to the preceding Figures. When executed by processing system 602 to provide projection functions, software 605 directs processing system 602 to operate as described herein for at least the various processes, operational scenarios, and sequences discussed in the foregoing implementations. Computing system 601 may optionally include additional devices, features, or functionality not discussed for purposes of brevity.

Referring still to FIG. 6, processing system 602 may comprise a micro-processor and other circuitry that retrieves and executes software 605 from storage system 603. Processing system 602 may be implemented within a single processing device but may also be distributed across multiple processing devices or sub-systems that cooperate in executing program instructions. Examples of processing system 602 include general purpose central processing units, graphical processing units, application specific processors, and logic devices, as well as any other type of processing device, combinations, or variations thereof.

Storage system 603 may comprise any computer readable storage media readable by processing system 602 and capable of storing software 605. Storage system 603 may include volatile and nonvolatile, removable and non-removable media implemented in any method or technology for storage of information, such as computer readable instructions, data structures, program modules, or other data. Examples of storage media include random access memory, read only memory, magnetic disks, optical disks, optical media, flash memory, virtual memory and non-virtual memory, magnetic cassettes, magnetic tape, magnetic disk storage or other magnetic storage devices, or any other suitable storage media. In no case is the computer readable storage media a propagated signal.

In addition to computer readable storage media, in some implementations storage system 603 may also include computer readable communication media over which at least some of software 605 may be communicated internally or externally. Storage system 603 may be implemented as a single storage device but may also be implemented across multiple storage devices or sub-systems co-located or distributed relative to each other. Storage system 603 may comprise additional elements, such as a controller, capable of communicating with processing system 602 or possibly other systems.

Software 605 (including video image projection process 606) may be implemented in program instructions and among other functions may, when executed by processing system 602, direct processing system 602 to operate as described with respect to the various operational scenarios, sequences, and processes illustrated herein. For example, software 605 may include program instructions for implementing a distraction therapy system as described herein.

In particular, the program instructions may include various components or modules that cooperate or otherwise interact to carry out the various processes and operational scenarios described herein. The various components or modules may be embodied in compiled or interpreted instructions, or in some other variation or combination of instructions. The various components or modules may be executed in a synchronous or asynchronous manner, serially or in parallel, in a single threaded environment or multi-threaded, or in accordance with any other suitable execution paradigm, variation, or combination thereof. Software 605 may include additional processes, programs, or components, such as operating system software, virtualization software, or other application software. Software 605 may also comprise firmware or some other form of machine-readable processing instructions executable by processing system 602.

In general, software 605 may, when loaded into processing system 602 and executed, transform a suitable apparatus, system, or device (of which computing system 601 is representative) overall from a general-purpose computing system into a special-purpose computing system customized to provide projection-based distraction therapy as described herein. Indeed, encoding software 605 on storage system 603 may transform the physical structure of storage system 603. The specific transformation of the physical structure may depend on various factors in different implementations of this description. Examples of such factors may include, but are not limited to, the technology used to implement the storage media of storage system 603 and whether the computer-storage media are characterized as primary or secondary storage, as well as other factors.

For example, if the computer readable storage media are implemented as semiconductor-based memory, software 605 may transform the physical state of the semiconductor memory when the program instructions are encoded therein, such as by transforming the state of transistors, capacitors, or other discrete circuit elements constituting the semiconductor memory. A similar transformation may occur with respect to magnetic or optical media. Other transformations of physical media are possible without departing from the scope of the present description, with the foregoing examples provided only to facilitate the present discussion.

Communication interface system 607 may include communication connections and devices that allow for communication with other computing systems (not shown) over communication networks (not shown). Examples of connections and devices that together allow for inter-system communication may include network interface cards, antennas, power amplifiers, radiofrequency circuitry, transceivers, and other communication circuitry. The connections and devices may communicate over communication media to exchange communications with other computing systems or networks of systems, such as metal, glass, air, or any other suitable communication media. The aforementioned media, connections, and devices are well known and need not be discussed at length here.

Communication between computing system 601 and other computing systems (not shown), may occur over a communication network or networks and in accordance with various communication protocols, combinations of protocols, or variations thereof. Examples include intranets, internets, the Internet, local area networks, wide area networks, wireless networks, wired networks, virtual networks, software defined networks, data center buses and backplanes, or any other type of network, combination of networks, or variation thereof. The aforementioned communication networks and protocols are well known and need not be discussed at length here.

While some examples provided herein are described in the context of a video project-based distraction therapy system for radiation therapy, it should be understood that the systems and methods described herein are not limited to such embodiments and may apply to a variety of other project-based scenarios and their associated systems. As will be appreciated by one skilled in the art, aspects of the present invention may be embodied as a system, method, computer program product, and other configurable systems. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The phrases "in some embodiments," "according to some embodiments," "in the embodiments shown," "in other embodiments," and the like generally mean the particular feature, structure, or characteristic following the phrase is included in at least one implementation of the present technology, and may be included in more than one implementation. In addition, such phrases do not necessarily refer to the same embodiments or different embodiments.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for," but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A video content projection system for distraction during radiation therapy comprising:
   a video source;
   a projector, located inside a radiation therapy room, communicatively coupled to the video source, wherein the projector receives the video content from the video source and emits a projection of the video content into a first end of a beam expander; and
   the beam expander, coupled to the projector, that receives the projection of the video content, increases a throw ratio of the projection to produce a modified projection of the video content, and emits the modified projection of the video content from a second end of the beam expander onto a first side of a radio-transparent screen, wherein:
   the beam expander comprises multiple lenses that focus the modified projection of the video content onto the first side of the radio-transparent screen and flip the projection of the video content such that the video content can be viewed in a non-reversed fashion on a second side of the radio-transparent screen by a patient on a radiation therapy couch during the radiation therapy; and
   the modified projection of the video content comprises a smaller projection image than the projection of the video content.

2. The video content projection system of claim 1, further comprising the radio-transparent screen, wherein the radio-transparent screen is mounted above the radiation therapy couch in the radiation therapy room and emanates the modified projection of the video content to the second side of the screen.

3. The video content projection system of claim 2, further comprising at least one set of wireless repeaters that communicate the video content from the video source to the projector, wherein the video source is located outside of the radiation therapy room.

4. The video content projection system of claim 3, further comprising an adjustable projector housing comprising a proximal end and a distal end, wherein the projector is attached to the distal end and the proximal end comprises a clamp via which the adjustable projector housing is secured in the radiation therapy room.

5. The video content projection system of claim 4, wherein:
the projector is mounted inside the radiation therapy room at a location where the projector will not perturb a radiation beam during the radiation therapy; and
the projector is a pico projector.

6. The video content projection system of claim 1, wherein the multiple lenses of the beam expander comprise at least one set of achromatic doublets, wherein the at least one set of achromatic doublets comprises a concave lens and a convex lens.

7. The video content projection system of claim 1, wherein a throw ratio (distance:width) of the modified projection of the video content is at least 6:1.

8. A video image projection-based distraction therapy system for radiation therapy comprising:
a projector, wherein the projector is located inside a radiation therapy room at a location where it does not interfere with radiation beams during the radiation therapy being administered to a patient on a radiation therapy couch and:
receives the video image from a video source; and
emits a projection of the video image onto a first lens on a first end of a beam manipulator;
the beam manipulator, coupled to the projector, that receives the projection of the video image on the first end, increases a throw ratio of the projection to produce a modified projection of the video image, and emits the modified projection of the video image from a second end of the beam manipulator onto a first side of a radio-transparent screen, wherein:
the beam manipulator comprises multiple lenses that focus the modified projection of the video image onto the first side of the radio-transparent screen and flip the projection of the video image such that the video image can be viewed in a non-reverse fashion on a second side of the radio-transparent screen by the patient on the radiation therapy couch; and
the modified projection of the video image comprises a smaller projection image than the projection of the video image; and
the radio-transparent screen, wherein the radio-transparent screen is mounted above the radiation therapy couch in the radiation therapy room and emanates the modified projection of the video image to the second side of the radio-transparent screen.

9. The video image projection-based distraction therapy system of claim 8, further comprising:
the video source; and
at least one set of wireless repeaters that communicate the video image from the video source to the projector, wherein the video source is located outside of the radiation therapy room.

10. The video image projection-based distraction therapy system of claim 8, wherein the throw ratio of the projection of the video image is less than 6:1 (distance:width).

11. The video image projection-based distraction therapy system of claim 8, further comprising an adjustable projector housing comprising a proximal end and a distal end, wherein the projector is attached to the distal end and the proximal end comprises a clamp via which the adjustable projector housing is secured in the radiation therapy room.

12. The video image projection-based distraction therapy system of claim 10, wherein a throw ratio of the modified projection of the video image is at least 6:1 (distance:width).

13. The video image projection-based distraction therapy system of claim 12, wherein the multiple lenses of the beam manipulator comprise at least one set of achromatic doublets, wherein the at least one set of achromatic doublets comprises a concave lens and a convex lens.

14. The video image projection-based distraction therapy system of claim 13, wherein the projector is a pico projector and the beam manipulator comprises a beam expander.

15. A method of operating a video content projection system for distraction during radiation therapy, the method comprising:
communicating the video content from a video source to a projector, wherein the video source is located outside of a radiation therapy room and the projector is located inside of the radiation therapy room;
receiving, by the projector, the video content from the video source;
projecting, by the projector, a projection of the video content into a first end of a beam expander coupled to the projector;
by the beam expander:
receiving the projection of the video content in the first end of the beam expander;
increasing a throw ratio of the projection to produce a modified projection of the video content; and
emitting the modified projection of the video content from a second end of the beam expander onto a first side of a radio-transparent screen;
wherein the beam expander comprises multiple lenses that focus the modified projection of the video content onto the first side of the radio-transparent screen and flip the projection of the video content such that the video content can be viewed in a non-reversed fashion on a second side of the radio-transparent screen by a patient on a radiation therapy couch during the radiation therapy; and
wherein the modified projection of the video content comprises a smaller projection image than the projection of the video content; and
displaying the video content on the second side of the radio-transparent screen in the non-reversed fashion.

16. The method of claim 15, wherein the radio-transparent screen is mounted above the radiation therapy couch and emanates the video content to the second side of the radio-transparent screen.

17. The method of claim 16, wherein communicating the video content from the video source to the projector comprises communicating the video content from the video source to the projector via at least one set of wireless repeaters.

18. The method of claim 15, wherein a throw ratio (distance:width) of the modified projection of the video content is at least 6:1.

19. The method of claim 15, wherein the projector is a pico projector and is mounted inside the radiation therapy room at a location where the projector will not perturb a radiation beam during the radiation therapy.

20. The method of claim 15, wherein the multiple lenses of the beam expander comprise at least one set of achromatic doublets, wherein the at least one set of achromatic doublets comprises a concave lens and a convex lens.

* * * * *